United States Patent
Mayer et al.

(10) Patent No.: US 8,916,037 B1
(45) Date of Patent: Dec. 23, 2014

(54) INSTRUMENT AND METHOD FOR MEASURING HIGH CONCENTRATIONS OF CARBON MONOXIDE IN A GASEOUS SAMPLE

(75) Inventors: Daniel W. Mayer, Wyoming, MN (US); Michael D. Howe, Blaine, MN (US)

(73) Assignee: Mocon, Inc., Minneapolis, MN (US)

( * ) Notice: Subject to any disclaimer, the term of this patent is extended or adjusted under 35 U.S.C. 154(b) by 1814 days.

(21) Appl. No.: 11/469,122

(22) Filed: Aug. 31, 2006

(51) Int. Cl.
 *G01N 27/413* (2006.01)
(52) U.S. Cl.
 USPC .................. 204/415; 205/782.5; 205/782
(58) Field of Classification Search
 USPC ............. 204/400–435; 205/775–794.5; 73/23.31–23.32
 See application file for complete search history.

(56) References Cited

U.S. PATENT DOCUMENTS

| | | | |
|---|---|---|---|
| 4,522,835 A * | 6/1985 | Woodruff et al. | 426/264 |
| 5,372,696 A * | 12/1994 | Kiesele et al. | 204/416 |
| 5,830,337 A * | 11/1998 | Xu | 204/400 |
| 6,338,266 B1 * | 1/2002 | Warburton | 73/23.2 |
| 6,370,940 B2 * | 4/2002 | Warburton | 73/23.21 |
| 6,936,147 B2 | 8/2005 | Prohaska et al. | |
| 2003/0085125 A1 | 5/2003 | Prohaska et al. | |
| 2003/0121781 A1 | 7/2003 | Prohaska et al. | |
| 2005/0126930 A1 | 6/2005 | Prohaska et al. | |

FOREIGN PATENT DOCUMENTS

| | | | |
|---|---|---|---|
| DE | 4019855 | * | 11/1992 |
| EP | 1304565 A2 | | 4/2003 |
| WO | WO01/36956 A1 | | 5/2001 |

* cited by examiner

*Primary Examiner* — Bach Dinh
(74) *Attorney, Agent, or Firm* — Sherrill Law Offices, PLLC

(57) ABSTRACT

An instrument and method for accurately measuring target analyte levels is a gas sample over an extended range. The instrument includes (i) a sensor effective for detecting the analyte, and (ii) a barrier film having limited permeability for the analyte covering the inlet orifice on the sensor for reducing the flux of analyte into the sensor. The method involves (a) sensing the flux of target analyte passing through the barrier film and into sensing contact with the sensor, and (b) reporting a concentration of analyte by multiplying a concentration value previously correlated to the sensed flux by the flux reduction factor of the barrier film.

18 Claims, 1 Drawing Sheet

INSTRUMENT AND METHOD FOR MEASURING HIGH CONCENTRATIONS OF CARBON MONOXIDE IN A GASEOUS SAMPLE

BACKGROUND

Carbon monoxide is known to react with components in meat and fish to maintain a consumer-preferred fresh-cut coloration of the meat or fish. For this reason carbon monoxide is often introduced into packaged meat and fish at concentrations of about 0.2% to 5% to enhance the products consumer appeal. Unfortunately, the coloration created by the use of excessive carbon monoxide can mask the normal visual indications of spoilage. Hence, the meat packaging industry, as well as those in the distribution chain, are seeking ways to monitor and control the concentration of carbon monoxide introduced into packaged meat and fish to attain a proper balancing of consumer preference for fresh colored meat and fish with the need for a visual indication of spoilage.

A wide range of sensors are known and available for detecting carbon monoxide levels, including electrochemical sensors, infrared sensors and tin oxide sensors. While each type of sensor possesses various combinations of benefits and detriments (e.g., level of resolution, cost, sensitivity to other variables such as temperature and humidity, etc.) such sensors are generally overly sensitive to other components in a gas sample or are subject to overrange at concentrations in excess of about 1,000 to 1,500 ppm (i.e., 0.1% to 0.15%). Hence, while such sensors are effective for detecting toxic levels of carbon monoxide in air, they are not suitable for use in measuring the concentration of carbon monoxide in environments having potentially high concentration of carbon monoxide, such as packaged meat and fish.

Accordingly, a substantial need exists for an inexpensive, high resolution sensor capable of accurately measuring carbon monoxide levels over an extended range.

SUMMARY OF THE INVENTION

A first aspect of the invention is an instrument comprising (i) a sensor effective for detecting an analyte and having an inlet orifice configured and arranged for allowing ingress of a sample gas into sensing contact with the sensor, and (ii) a barrier film having limited permeability for the analyte and covering the inlet orifice for reducing the flux of analyte through the inlet orifice and into sensing contact with the sensor.

A second aspect of the invention is a method of measuring the concentration of an analyte in a gas. The method includes the steps of (a) obtaining an instrument comprising (i) a sensor effective for detecting an analyte and having an inlet orifice configured and arranged for allowing ingress of a sample gas to be tested into sensing contact with the sensor, and (ii) a barrier film having limited permeability for the analyte and covering the inlet orifice for reducing the flux of analyte through the inlet orifice and into sensing contact with the sensor by a known flux reduction factor, (b) placing a gas to be tested into fluid communication with the barrier film covering the inlet orifice, (c) sensing a flux of analyte passing through the barrier film and into sensing contact with the sensor, and (d) reporting a concentration of analyte by multiplying a concentration value previously correlated to the sensed flux by the flux reduction factor of the barrier film.

The instrument and method are particularly well suited for testing the concentration of carbon monoxide in gas withdrawn from packaged meat, fish or poultry.

DETAILED DESCRIPTION OF THE INVENTION INCLUDING A BEST MODE

Nomenclature

10 Instrument
20 Sensor
30 Sensor Housing
38 Inlet Orifice Through Sensor Housing
39 Outlet Orifice Through Sensor Housing
41 Anode or Sensing Electrode
42 Cathode or Counter Electrode
50 Separator
60 Current Collection Leads
61 Sensor Pins
70 Sample Container
71 Retention Chamber Defined by Sample Container
78 Inlet Port Through Sample Container
79 Outlet Port Through Sample Container
80 Barrier Film
81 Outward Facing Major Surface of Barrier Film
82 Inward Facing Major Surface of Barrier Film

Instrument

Figure 1:
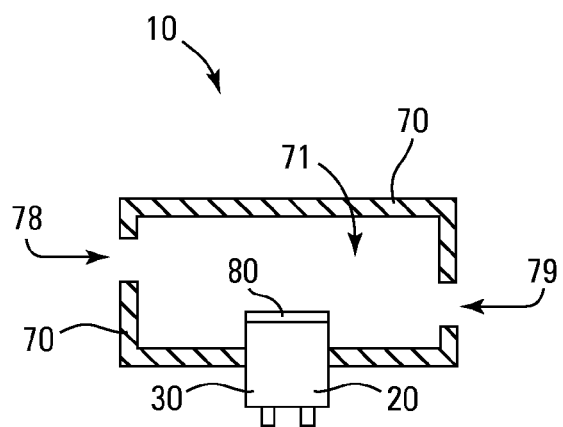
FIG. 1 is a side view of one embodiment of the invention with the sample container shown in cross-section to facilitate viewing of internal features and components of the invention.
Figure 2:
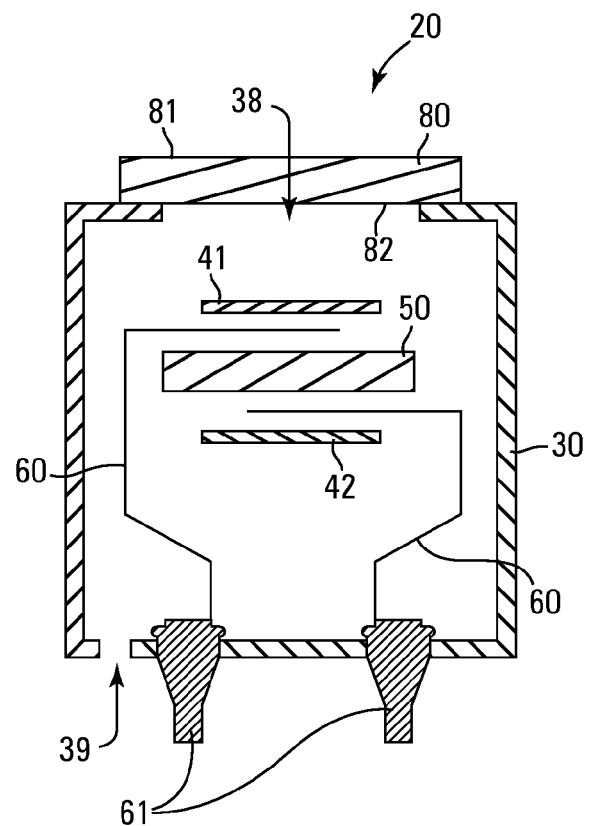
FIG. 2 is an enlarged cross-sectional side view of the sensor and barrier film shown in FIG. 1 with the electrodes, separator plate and current collection leads separated to facilitate viewing.

As shown in FIGS. 1 and 2, a first aspect of the invention is an instrument 10 having (i) a sample container 70 defining a retention chamber 71 for sealingly retaining a gas sample of interest, (ii) a sensor 20 for sensing a target analyte in the gas sample, and (iii) a barrier film 80 sealingly positioned over the inlet orifice 38 of the sensor 20 for separating the retention chamber 71 and the sensor 20. The barrier film 80 has a rate limiting permeability for the target analyte so as to be effective for reducing the flux of target analyte passing from the gas sample in the retention chamber 71 through the inlet orifice 38 and into sensing contact with the sensor 20. This allows the sensor 20 to provide quick and accurate measurements of target analyte concentration in the gas sample even when the concentration of target analyte in the sample far exceeds the overrange concentration of the sensor 20.

The sensor 20 may be selected from any of the well known types of sensors for sensing a target analyte in a sample gas, including specifically but not exclusively, infrared sensors, electrochemical sensors, semiconductor sensors, photoionization sensors, tin oxide sensors, etc. While application specific, electrochemical sensors are particularly well suited for use in the invention as electrochemical sensors often provide superior resolution at modest cost but are found unsuitable for use as they have a limited useful range. The instrument 10 significantly expands the useful range of the sensor 20 and therefore permits deployment of electrochemical sensors in applications once thought beyond the reach of such sensors.

As shown in FIG. 2, standard electrochemical sensors 20 include an anode or sensing electrode 41, a cathode or counter electrode 42, an electrolyte (not shown) between the anode 41 and cathode 42 and current collection leads 60 between the anode 41 and cathode 42 for sensing any current generated within the sensor 20 by the oxidation or reduction of analyte within the sensor 20 and sending an appropriate electrical signal to the sensor pins 61. A separator 50 is typically provided between the interior-facing major surfaces (unnumbered) of the anode 41 and cathode 42. The separator 50 serves as a mechanical separator for creating and maintaining a gap (unnumbered) between the anode 41 and the cathode 42, and as a supporting substrate for the electrolyte. Since the separator 50 is in direct physical contact with both the anode 41 and the cathode 42, the separator 50 must be constructed from an electrically insulating material to prevent the generation of false signals. The separator 50 must also be sufficiently porous to permit free passage of target analyte through the separator 50. By way of example, a suitable carbon monoxide sensor is a 4CO CITICEL® unfiltered sensor available from City Technology Ltd of Portsmouth, England.

A housing 30 protectively surrounds the components of the sensor 20 and assists in retaining the components in a fixed, dimensionally stable position relative to one another while permitting controlled flow of a gaseous sample to be tested through an inlet orifice 38 in the housing 30 and into contact with the anode 41 and cathode 42. An outlet orifice 39 should also be provided through the housing 30 for permitting egress of gaseous reaction products from the sensor 20. It has been discovered that the barrier film 80 not only reduces the flux of target analyte into the sensor 20 but can also reduce the flux of reaction product(s) out of the sensor 20, resulting in the development of a positive pressure gradient across the barrier film 80. Such positive gradient can interfere with performance of the instrument 10 and needs to be eliminated in order to maintain the desired level of accuracy. A further benefit obtained by providing an outlet orifice 39 through the housing 30 is the ability for environmentally available reactants other than the target analyte (typically $O_2$) to diffuse into the sensor 20 through the outlet orifice 39 in the event an insufficient concentration of the reactant is available in the gaseous sample to be tested and/or the barrier film 80 is not sufficiently permeable to the reactant. It is noted that an outlet orifice 39 permitting passage of environmental air into the sensor 20 should not be provided through the housing 30 when the surrounding air contains any appreciable concentration of the target analyte as target analyte may be introduced onto the sensor 20 through the outlet orifice 39 and thereby taint the measurements obtained by the sensor 20.

A container 70 defining a retention chamber 71 is provided for sealingly retaining a sample of the gas to be tested. The container 70 has an inlet port 78 and an outlet port 79 for permitting the introduction of fresh gas samples into and the flushing of spent gas samples out from the retention chamber 71. The sensor 20 is positioned relative to the container 70 so that the outward facing major surface 81 of the barrier film 80 is exposed to any gas sample within the retention chamber 71.

The instrument 10 can be effectively employed to sense a wide range of analytes, including specifically but not exclusively ammonia, carbon dioxide, carbon monoxide, chlorine, ethylene oxide, hydrogen, hydrogen chloride, hydrogen cyanide, hydrogen sulfide, methane, nitric oxide, nitrogen dioxide, oxygen, ozone and sulfur dioxide. The instrument 10 is particularly well suited for sensing carbon monoxide at concentrations up to about 5% using standard commercially available carbon monoxide sensors. Use of the instrument 10 for sensing carbon monoxide at concentrations in excess of about 5% tends to result in unreliable data as the flux of carbon monoxide into the sensor 20 tends to exceed the overrange capacity of the sensor 20 despite the presence of the barrier film 80.

The barrier film 80 is positioned over the inlet orifice 39 through the sensor housing 30 and inward facing major surface 82 of the barrier film 80 sealingly attached to the housing 30. The barrier film 80 constructed from a material capable of modestly reducing the flux of target analyte from the retention chamber 71 into sensing contact with the sensor 20. For most applications, a flux reduction factor of about 5 to 100 is desired. This reduction in flux effectively equates to a reduction in the efficiency coefficient of the sensor 20, thereby allowing the sensor 20 to be used when the actual concentration of the target analyte exceeds the overrange concentration of the sensor 20. The reading from the sensor 20 need merely be multiplied by the empirically derived flux reduction factor of the barrier film 80 in order to compensate for the reduced flux observed by the sensor 20. By way of example, a suitable barrier film 80 for carbon monoxide is polydimethylsiloxide sheathing available from FMI Incorporated of Elk Grove Village, Ill. Polydimethylsiloxide sheathing is particularly suitable for such use as the sheathing can provide a flux reduction factor of about 10 to 50 while maintaining a good response time, and does not significantly impede the movement of $O_2$—a necessary reactant for oxidizing CO within the sensor 20—into the sensor 20.

Without intending to be unduly limited thereby, it is believed that the barrier film 80 should be permeable rather than porous with respect to the target analyte as the flux through a porous barrier film 80 can be impacted by many other variables such as temperature, pressure and humidity, while permeability is relatively stable regardless of changes in such variables.

EXAMPLES

Example 1

A gas sample is withdrawn from a package of red-meat believed to have a concentration of between about 0.2% and about 1% carbon monoxide and introduced into the retention chamber of an instrument equipped with a carbon monoxide sensor capable of effectively sensing carbon monoxide between a concentration of 0 to 500 ppm (0 to 0.05%) up to a maximum concentration of about 1,500 ppm (0.15%). A medical grade polydimethylsiloxane film having a known flux reduction factor of twenty (20) is adhesively attached over the inlet opening in the sensor housing.

The sensor is activated and a steady state flux of CO molecules/sec is detected by the sensor. This sensed flux is automatically correlated to a concentration value based upon previously empirically derived correlation values between sensed flux and concentration, and the correlated concentration value multiplied by the flux reduction factor to achieve a final reportable value of CO concentration in the gas sample.

We claim:

1. An instrument comprising (i) a sensor effective for detecting and measuring a concentration of carbon monoxide in a sample gas and having an inlet orifice configured and arranged for allowing ingress of a at least a portion of a sample gas into sensing contact with the sensor, and (ii) a barrier film having limited permeability for carbon monoxide Covering the inlet orifice for reducing the flux of carbon monoxide through the inlet orifice and into sensing contact with the sensor by a known factor of between 5 and 100, whereby the instrument can effectively measure a concentration of carbon monoxide in a sample gas up to a concentration of 2,000 ppm.

2. The instrument of claim 1 further comprising a retention chamber in fluid communication with the inlet orifice through the barrier film, and having an inlet port configured and arranged for allowing ingress of a sample gas into the retention chamber.

3. The instrument of claim 1 further comprising an outlet orifice effective for permitting egress of gaseous reaction products from the sensor.

4. The instrument of claim 1 wherein the sensor is an electrochemical sensor.

5. The instrument of claim 1 wherein the barrier film reduces the flux of carbon monoxide into sensing contact with the sensor by a known factor of between 10 and 50.

6. The instrument of claim 1 wherein the barrier film is constructed from a polysiloxane.

7. The instrument of claim 6 wherein the polysiloxane is polydimethylsiloxane.

8. A method of measuring concentration of carbon monoxide in a gas, comprising the steps of:
   (a) obtaining the instrument of claim 1,
   (b) placing a gas to be tested into fluid communication with the barrier film covering the inlet orifice, wherein the anticipated concentration of carbon monoxide in the gas to be tested is up to 0.2%,
   (c) sensing a flux of carbon monoxide passing through the barrier film and into sensing contact with the sensor, and
   (d) reporting, a concentration of carbon monoxide by multiplying a concentration value previously correlated to the sensed flux by the flux reduction factor of the barrier film.

9. The method of claim 8 wherein the instrument further comprises a retention chamber in fluid communication with the inlet orifice through the barrier film, and the gas is placed into fluid communication with the barrier film covering the inlet orifice by introducing the gas into the retention chamber.

10. The method of claim 8 wherein the instrument further comprises an outlet orifice effective for permitting egress of gaseous reaction products from the sensor.

11. The method of claim 8 wherein the sensor is an electrochemical sensor.

12. The method of claim 8 wherein the barrier film reduces the flux of carbon monoxide into sensing Contact with the sensor by a known factor of between 10 and 50.

13. The method of claim 8 wherein the barrier film is constructed from a polysiloxane.

14. The method of claim 13 wherein the polysiloxane is polydimethylsiloxane.

15. The method of claim 8 wherein the gas to be tested is withdrawn from packaged meat, fish or poultry.

16. A method of measuring concentration of carbon monoxide in a gas, comprising the steps of:
   (a) obtaining the instrument of claim 1,
   (b) placing a gas to be tested into fluid communication with the barrier film covering the inlet orifice, wherein the concentration of carbon monoxide in the gas to be tested is between about 0.2% and about 5%,
   (c) sensing a flux of carbon monoxide passing through the barrier film and into sensing contact with the sensor, and
   (d) reporting a concentration of carbon monoxide by multiplying a concentration value previously correlated to the sensed flux by the flux reduction factor of the barrier film.

17. The instrument of claim 1 wherein the instrument can effectively measure a concentration of carbon monoxide in a sample gas up to a concentration of 50,000 ppm.

18. A method of measuring concentration of carbon monoxide in a gas, comprising the steps of:
   (a) obtaining the instrument of claim 17,
   (b) placing a gas to be tested into fluid communication with the barrier film covering the inlet orifice, wherein the anticipated concentration of carbon monoxide in the gas to be tested is up to 5%,
   (c) sensing a flux of carbon monoxide passing through the barrier film and into sensing contact with the sensor, and
   (d) reporting a concentration of carbon Monoxide by multiplying a concentration value previously correlated to the sensed flux by the flux reduction factor of the barrier film.

* * * * *